United States Patent

Caubere et al.

[11] Patent Number: 5,442,080
[45] Date of Patent: Aug. 15, 1995

[54] PROCESS FOR PREPARING POLYAZIDO ALCOHOLS AND POLYAMINO ALCOHOLS AND APPLICATION TO THE PREPARATION OF POLYAZIDOTHIOLS AS DERIVATIVES THEREOF

[75] Inventors: Paul Caubere, Nancy; Herve Forconi, Longjumeau, both of France

[73] Assignee: Etat Francais represente par le Delegue General pour l'Armement, Paris, France

[21] Appl. No.: 980,217

[22] Filed: Nov. 23, 1992

[30] Foreign Application Priority Data

Nov. 21, 1991 [FR] France ................. 91 14541

[51] Int. Cl.⁶ .............................................. C07F 9/28
[52] U.S. Cl. ................................... 552/8; 552/10
[58] Field of Search ............................. 552/8, 10

[56] References Cited

PUBLICATIONS

Patterson, *A French-English Dictionary for Chemists*, 2nd Ed., pp. 38–39 (1954).
Cotton, et al., *Advanced Inorganic Chemistry*, 2nd Ed., p. 331 (1966).
*Hach's Chemical Dictionary*, 4th Ed., p. 457 (1972).
*McGraw-Hill Dictionary of Chemical Terms*, Sybil Parker, ed. p. 380 (1984).
Mansion I. E. *Harrap's Standard French & English Dictionary*, p. A:87 (1980).
Edgar R. Wilson et al., *J. Chem. Eng. Data*, Oct. 1982, vol. 27, No. 4, pp. 472–473.
C. A. VanderWerf et al., *J. Amer. Chem. Soc.*, Mar. 6, 1954, vol. 76, No. 4, pp. 1231–1235.

*Primary Examiner*—Johann Richter
*Assistant Examiner*—Kimberly J. Kestler
*Attorney, Agent, or Firm*—Oliff & Berridge

[57] ABSTRACT

The invention concerns a process of preparation of the polyazido alcohols by reaction of a polysubstituted oxirane having in position β a nucleofuge group with a metal nitride, characterized in that the reaction is performed in an aqueous medium.

The oxirane formula is:

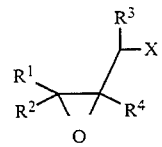

in which X represents a nucleofuge substituent, R1 represents an atom of hydrogen, a lower alkyl group substituted or not by a halogen, an aryl group possibly substituted, R2 and R3 represent an atom of hydrogen, a lower alkyl radical possibly substituted, an aryl group possibly substituted, R4 represents an atom of hydrogen, a lower alkyl group possibly substituted, an aryl group possibly substituted by an alkoxy group. Application to the preparation of polyamino alcohols, ureas, polyazidothiols and binding compositions for propergols.

18 Claims, No Drawings

PROCESS FOR PREPARING POLYAZIDO ALCOHOLS AND POLYAMINO ALCOHOLS AND APPLICATION TO THE PREPARATION OF POLYAZIDOTHIOLS AS DERIVATIVES THEREOF

The present invention concerns the preparation of polyazido alcohols, as well as their applications to the preparation of derivatives and binding compositions for propergols.

More particularly, the invention applies to the obtention of polyazido alcohols by reaction of polyazidation of a polysubstituted oxirane having a nucleofuge group in position $\beta$, in aqueous phase.

The polyazido alcohols appear to be practically very useful, as they bear at the same time energetic functions and a function allowing them to be transplanted on another monomer molecule or on a polymer.

Thus, due to their energetic properties, they can be used in the fabrication of polymers used in binders for propergols. This binder is integrated into the propergol in order to give it flexibility and mechanical resistance. In addition to its mechanical qualities, it is recommended for it to bring the energetic groups intended to improve the propulsive qualities of the propergol.

The most often used energetic groups are the azide, the nitrated, fluoroaminated, fluoronitrated groups. The monomers used to prepare the binding polymer are notably the cyclic ethers and, among them, the epoxides or oxiranes bearing nitro or nitride functions.

Thus, the compounds rich in nitrogen and, particularly those containing several $N_3$ azide groups are of special interest in the fabrication of propergols.

Polyglycidylazides prepared by reaction of mineral azide, such as the sodium nitride $N_a N_3$, with polyepichlorhydrin polymers with oxhydril termination are described in French patent 2638751.

According to the invention, the polyazidoalcohols to be polymerized later on, are prepared first.

The aminated derivatives of the polyazido alcohols are currently used in medicinal chemistry and more particularly in renal radiopharmaceutical metal chelation.

The process according to the invention also represents an easy path to polyazido alcohols derivatives such as the ureas and polyazidothiols.

Several studies related to the azidation of epoxide compounds among which the study performed by M. B. Frankel; J. Chem. Eng. Data, 1982, 27, 472 mention the opening of the oxiranic cycle by the azide ion of the sodium azide in organic medium, according to a reaction of the nucleophilic bimolecular type reaction called $SN_2$ leading to monoazido alcohols. According to the literature, the preparation of polyazido alcohols is much more difficult.

C. A. VANDER WERF, R. Y. HEISLER and W. E. Mc EWEN in J.Amer Chem. Soc., 1954, 76, 1231–1235 describe the reaction, in the presence of an organic solvent, of the sodium azide with several cyclic epoxides such as the cloclohexne oxide or the cyclopentene oxide and of linear ones such as propylene and diisobutylene oxide, butadiene oxide and epichlorhydrin. In the case of the epichlorhydrin, the authors point out the obtention of 1,3-diazido 2-propanol in the dioxan and of an unidentified by-product.

For the oxiranes whose general formula is

where R is a substituent, these authors showed that the azide ion attacks the less substituted carbon of the oxiranic cycle according to a reaction of the nucleophilic bimolecular $SN_2$ type to lead to diazido alcohols.

Therefore, the major disadvantage of this method of synthesis of the polyazido alcohols in organic medium is to lead in majority to an azided oxirane $\beta$, as the opening of the oxiranic cycle does not take place.

Nevertheless, in the cases when the polyazidation is produced by the opening of the oxiranic cycle of a substituted oxiran $\beta$, usually a certain quantity of the starting product which did not react is left, or if the reaction is selective and produces a polyazido alcohol only, it appears to have a low yield.

The goal of the invention is to eliminate these disadvantages by offering an easy and selective process of preparation of polyazido alcohols, with a high yield. Moreover, the process has been generalized to polysubstituted oxiranes.

In that order, the goal of the invention is a process of preparation of polyazido alcohols by reaction of a polysubstituted oxirane having a nucleofuge group in position $\beta$ with a metal azide, characterized in that the reaction takes place in aqueous medium.

The solvent must favour the ionic transfers between the various phases and must be dissociating enough to allow the reaction. The low or non polar solvents favour the azide reactivity; the halogened solvents as well as the aprotic solvents are known to allow a good dissociation of the ions. The dipolar aprotic solvents are efficient for the ion extraction. Lastly, the protic solvents, as well as water, are convenient to the nucleophilic substitutions but they might cause the oxirane to open.

Unexpectedly, it appears that water is the convenient solvent. The here-under table shows the results obtained during the epichlorhydrin diazidation (1 equivalent)

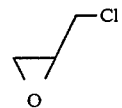

by the sodium nitride (4 equivalents), in the presence of a catalyst (tricaprylyl methylammonium chloride), depending on the used solvent.

| solvent | temperature (°C.) | 1-azido, 2.3-epoxy propane yield % | 1,3-diazido 2-propanol yield % |
|---|---|---|---|
| hexadecane | 95 | 0 | 0 |
| dioxane | 80 | 32 | — 0 |
| benzene | 80 | 60 | 0 |
| methylene chloride | 40 | 44 | 0 |
| dichloroethane | 40 | 42 | 0 |
| tetrahydrofuran | 80 | 0 | 39 |
| water | 100 | 0 | 90 |

Water appears to be the only solvent which gives a selective diazidation with a high yield.

Thus, the reaction appears to be perfectly selective as it exclusively produces polyazido alcohols with a very high yield.

The oxirane formula is

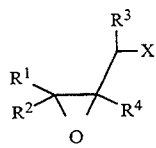

in which X represents a nucleofuge substituent, $R_1$ represents an atom of hydrogen, a lower alkyl group substituted or not by a halogen, an aryl group possibly substituted, $R_2$ represents an atom of hydrogen, a lower alkyl radical possibly substituted, an aryl group possibly substituted, $R_3$ represents an atom of hydrogen, a lower alkyl group possibly substituted, an aryl group possibly substituted, $R_4$ represents an atom of hydrogen, a lower alkyl group possibly substituted, an aryl group possibly substituted by an alkoxy groups, Preferably, the used azide is the sodium azide, the nucleofuge group is an atom of halogen, a tosylate radical or a mesylate radical.

Advantageously, the reaction is performed in the presence of a phase transferring catalyst, thus increasing the nucleophilic availability of the $N_3^-$ group of the sodium azide.

The catalyst is chosen among the quaternary ammonium salts, the tricaprylylmethylammonium chloride, which, in addition is the most inexpensive, appears here as being the catalyst which gives the best results. The cryptates as well as the phosphonium salts are also convenient.

The hereunder table shows the influence of the nature of the catalyst on the yield of the reaction when the sodium azide (4 equivalents) is made to react on epychlorhydrin (1 equivalent) in aqueous medium (0, 20 equivalents of water) at 80° C.

| Catalyst | Yield in 1,3-diazido 2-propanol (%) |
|---|---|
| None | 38 |
| Tricaprylylmethylammonium chloride | 90 |
| Benzyltrimethylammonium bromide | 72 |
| Methyltrialkyl ($C_8$-$C_{10}$) ammonium chloride | 72 |
| Tetraethylammonium bromide | 72 |
| Tetraethylammonium chloride | 69 |
| Tetrabutylammonium bromide | 84 |
| Tetrabutylammonium chloride | 54 |
| Cetylpyridinium chloride | 60 |
| Hexadecyl trimethylammonium bromide | 57 |
| Hexadecyl tributylphosphonium bromide | 57 |
| Tetrabutylphosphonium bromide | 69 |
| Tetrabutylphosphonium chloride | 70 |
| 2,5,8,11,14 Pentaoxapentadecane tetraglyme | 65 |
| 1,4,7,10,13,16-hexaoxacyclo-octadecane | 73 |
| Methyl triphenylphosphonium bromide | 61 |

The tricaprylylmethylammonium appears to be the catalyst which allows to obtain the best yield.

The temperature of the reaction has a significant influence on the speed of formation of the polyazido alcohols. Preferably, the operation takes place at a temperature between 20° C. and 100° C.

In the case of the synthesis of the diazidopropanols, the preferred temperature is 80° C.

4 equivalents is the quantity of sodium azide leading to the best results.

Under the previously mentioned conditions, the time of the reaction is approximately 72 hours for all the starting product to disappear.

The observed reaction is schematized hereunder:

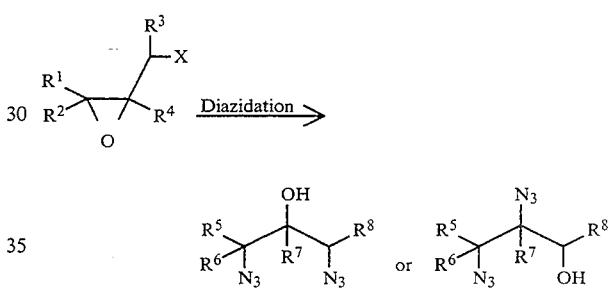

The $R_1$, $R_2$, $R_3$, $R_4$ and X substituents have the previously indicated meanings.

Usually, the $R_5$ substituent is identical to $R_1$, $R_6$ is identical to $R_2$, $R_7$ is identical to $R_4$, and $R_8$ is identical to $R_3$. Two families of new compounds, the 1,3-diazido alcohols and the 1,2-diazido alcohols are obtained, depending on the $R_1$-$R_4$ substituents selected In the case of the epichlorohydrin, where $R_1$-$R_4$ represent atoms of hydrogen and X an atom of chlorine, a 1,3-diazido alcohol is obtained according to a $SN_2$ type reaction:

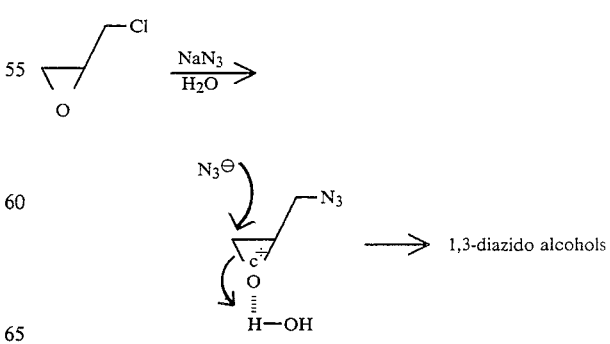

With the epibromhydrin bearing a $R_1$ substituent, a 1,2-diazido alcohol is obtained.

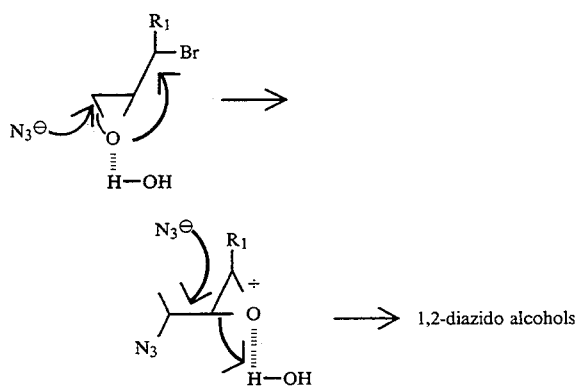

According to the invention, the polyazido alcohols are very energetic and they must be handled with the usual care. Distillation must be avoided as much as possible. It is recommended neither to submit them to shocks nor to abruptly increase their temperature.

The polyazido alcohols obtained according to the process of the invention are easily reduced by catalytic hydrogenation in the presence of palladium on carbon into polyamino alcohols, this giving an easy path of access to these last compounds. In the case of 1,3-diazido alcohols the reaction is as follows:

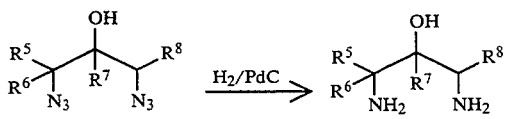

Similarly, later on it is very easy to transform the polyaminoalcohols into their corresponding ureas by reaction with the phosgene according to the following scheme with regards to the 1,2-diamino alcohols.

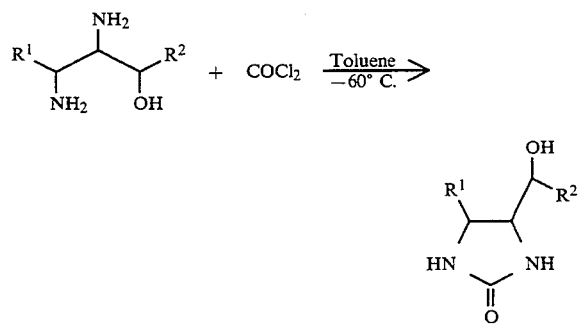

It might also be of interest to prepare polyazidothiols starting from polyazido alcohols obtained by the process of the invention. First, the chlorinated derivative of the polyazido alcohols will be synthetized by addition of thionyl chloride in the presence of pyridine in the chloroform. The shift to the thiol derivative is then performed by reaction of the obtained product with sodium hydrosulfide in the presence of soda and methanol.

Nevertheless, the most interesting application of the polyazido alcohols is the preparation of binding compositions for propergols, thanks to the energetic properties offered by the azide groups.

Other characteristics and advantages of the invention will appear in the following description of non limitative examples.

EXAMPLE 1

The Diazidation of the epichlorhydrin

In a 100 ml Woulff bottle equipped with a magnetic stirrer, a thermometer, a cooler, and a Mariotte's bulb, 4 equivalents (200 mM) of sodium azide $N_a N_3$, 0.2 equivalent (10 mM) of tricaprylylmethylammonium chloride and 1 equivalent of epichlorhydrin (50 mM) are mixed in 60 ml of water. The reactional medium is stirred for 72 hours at 80° C. The organic phase is extracted with methylene chloride, washed and dried over magnesium sulfate $MgSO_4$. Once the solvents are evaporated, the products are separated by flash chromatography with the use of acetylether/petroleum ether mixtures. 1,3-diazido 2-propanol is obtained with a 93% yield. The product is characterized by R.M.N and infrared spectroscopy.

IR (film between Na Cl tablet)
OH strips: (3000–3700) cm$^{-1}$
$N_3$ strips: (1890–2320) cm$^{-1}$
RMN $^1$H (CDCl$_3$), 60 MHz
3.10 (s, 1, OH exchanged with D$_2$O, d with DMSO).
3.30–3.50 (d, 4, CH$_2$N$_3$), 3.60–4.10 (m, 1, CHOH)
RMN $^{13}$C (CDCl$_3$), 400 MHz
53.70 (CH$_2$N$_3$, 69.43 (CHO)

Diazidation of oxiranes whose formula is the following

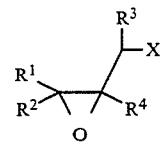

The mode of operation is similar to the one of example 1. Diazido alcohols whose formula is the following are obtained:

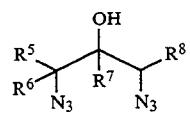

according to the examples 2–17 of the following table

| NUMBER | NATURE OF OXIRANE | | | | | NATURE OF THE FORMED PRODUCT | | | | YIELD (%) |
| --- | --- | --- | --- | --- | --- | --- | --- | --- | --- | --- |
| | R$^1$ | R$^2$ | R$^3$ | R$^4$ | X | R$^5$ | R$^6$ | R$^7$ | R$^8$ | |
| 2 | H | H | H | H | Cl | H | H | H | H | 93 |
| 3 | H | H | CH$_3$ | H | Br | H | H | H | CH$_3$ | 79 |
| 4 | H | CH$_3$ | H | H | Cl | H | H | H | CH$_3$ | 71 |
| 5 | CH$_3$ | CH$_3$ | H | H | Br | CH$_3$ | CH$_3$ | H | H | 87 |
| 6 | C$_6$H$_5$ | H | H | H | Cl | C$_6$H$_5$ | H | H | C$_6$H$_5$ | 74 |
| 7 | H | H | H | CH$_3$ | Cl | H | H | CH$_3$ | H | 70 |
| 8 | H | H | H | C$_2$H$_5$ | Cl | H | H | C$_2$H$_5$ | H | 78 |

-continued

| NUMBER | NATURE OF OXIRANE | | | | | NATURE OF THE FORMED PRODUCT | | | | YIELD (%) |
|---|---|---|---|---|---|---|---|---|---|---|
| | $R^1$ | $R^2$ | $R^3$ | $R^4$ | X | $R^5$ | $R^6$ | $R^7$ | $R^8$ | |
| 9 | H | H | H | $nC_4H_9$ | Cl | H | H | $nC_4H_9$ | H | 88 |
| 10 | H | H | H | $nC_8H_{17}$ | Cl | H | H | $nC_8H_{17}$ | H | 84 |
| 11 | H | H | H | $C_6H_5$ | Cl | H | H | $C_6H_5$ | H | 80 |
| 12 | H | H | H | $C_6H_5pOCH_3$ | Cl | H | H | $C_6H_5pOCH_3$ | H | 30 |
| | | | | | | H | H | $C_6H_5pOH$ | H | 40 |
| 13 | $CH_3$ | $C_6H_5$ | $C_6H_5$ | H | Br | $CH_3$ | $C_6H_5$ | H | $C_6H_5$ | 79 |
| 14 | $CH_2Cl$ | H | H | H | Cl | H | H | H | $CH_2Cl$ | 54 |
| 15 | H | H | H | H | I | H | H | H | H | 67 |
| 16 | H | H | H | H | (1) $OM_s$ | H | H | H | H | 93 |
| 17 | H | H | H | H | (2) $OT_s$ | H | H | H | H | 56 |

(1) $OM_s$ is the $CH_3$—$SO_3$ radical (mesylate)
(2) $OT_s$ is the $pCH_3C_6H_4$—$SO_3$ (p-toluene sulfonate or tosylate)

EXAMPLES 18–22

If sodium azide reacts, according to the mode of operation of example 1, on oxiranes whose formula is the following:

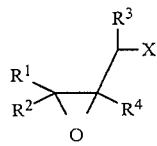

diazido alcohols with the following formula are obtained:

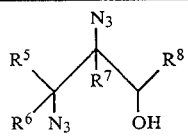

according to the reaction

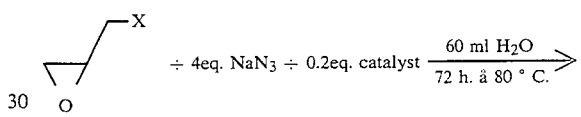

| NUMBER | NATURE OF OXIRANE | | | | | NATURE OF THE FORMED PRODUCT | | | | YIELD % |
|---|---|---|---|---|---|---|---|---|---|---|
| | R1 | R2 | R3 | R4 | X | R5 | R6 | R7 | R8 | |
| 18 | $CH_3$ | H | $CH_3$ | H | Br | $CH_3$ | H | H | $CH_3$ | 67 |
| 19 | $C_2H_5$ | H | $CH_3$ | H | Br | $C_2H_5$ | H | H | $CH_3$ | 76 |
| 20 | $C_2H_5$ | H | $C_6H_5$ | H | Br | $C_2H_5$ | H | H | $C_6H_5$ | 69 |
| 21 | $nC_8H_{17}$ | H | $CH_3$ | H | Br | $nC_8H_{17}$ | H | H | $CH_3$ | 86 |
| 22 | $nC_8H_{17}$ | H | $C_6H_5$ | H | Br | $nC_8H_{17}$ | H | H | $C_6H_5$ | 63 |

From these here-above examples 1–22 it emerges that: —the diazido alcohols are obtained with excellent yields —the two families of azido alcohols, i.e. the 1,3-diazido alcohols and the 1,2-diazido alcohols are never formed simultaneously. Obtaining one family or the other depends only on the structure of the starting oxirane.

It is noteworthy that, during the diazidation of the compound 12, a demethylation is observed which might be due to the formation of azothydric acid $HN_3$ in situ, or to a nucleophilic substitution.

The yield of the diazidation reaction is influenced by the nature of the nucleofuge substituent located in β in the oxirane epoxy group. The best results are reached with the chlorine and mesylate as shown in the following table related to oxiranes whose formula is the following:

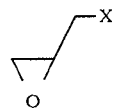

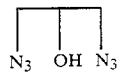

Surprisingly, no notable hydrolyzation of the oxirane in aqueous medium is observed, even with the epiiodhydrin which is very reactive.

| NATURE OF OXIRANE | |
|---|---|
| | Formed product YIELD (%) |
| X is Cl | 90 |
| X is Br | 76 |
| X is I | 67 |
| X is OMs | 93 |
| X is OTs | 56 |

EXAMPLE 23

Synthesis of polyamino alcohols.

By a classical technics of hydrogenation, the diazido alcohols are reduced into the ethanol with the use of Pd/C at 10% as a catalyst under a hydrogen atmosphere.

When the reaction is completed, the reactional medium is filtered on Celite 545 and the solvent evaporates. The diamino alcohols are obtained with a sufficient purity then the purification is useless. They all are gums or viscous liquids. The hereunder table shows the results reached when reducing the diazido alcohols of the examples 2–17.

| NATURE OF OXIRANE Example N° | DIASIDO-ALCOHOL NATURE Example N° | YIELD IN POLYAMINO-ALCOHOLS |
|---|---|---|
| 2 | 2 | 95 |
| 3 | 3 | 95 |
| 4 | 4 | 95 |
| 5 | 5 | 89 |
| 6 | 6 | 96 |
| 7 | 7 | 91 |
| 8 | 8 | 95 |
| 9 | 9 | 92 |
| 10 | 10 | 92 |
| 11 | 11 | 78 |
| 12 | 12a/12B | 85/81 |
| 13 | 13 | 97 |
| 14 | 14 | 95 |
| 18 | 18 | 91 |
| 19 | 19 | 92 |
| 20 | 20 | >99 |
| 21 | 21 | 92 |
| 22 | 22 | >99 |

EXAMPLE 24

Synthesis of ureas

In a 100 ml Woulff bottle containing 1 equivalent of polyamino alcohol, diluted in 50 ml of toluene, the following is added: a −60° C., 0.5 equivalent of phosgene in a 20% solution in toluene. The mixture is left at room temperature, stirred for two days at the room temperature and evaporates. Thus the urea, purified by washing in chloroform is obtained. The table shows the yields obtained in the following examples:

| POLYAMINOALCOHOLS | FORMED UREA | YIELD (%) |
|---|---|---|
| CH$_3$—CH(NH$_2$)—CH(NH$_2$)—CH(OH)—CH$_3$ | CH$_3$—HC—CH—CHOH—CH$_3$ with HN-C(=O)-NH ring | 93 |
| C$_2$H$_5$—CH(NH$_2$)—CH(NH$_2$)—CH(OH)—CH$_3$ | nC$_2$H$_5$—HC—CH—CHOH—CH$_3$ with HN-C(=O)-NH ring | 95 |
| C$_2$H$_5$—CH(NH$_2$)—CH(NH$_2$)—CH(OH)—C$_6$H$_5$ | nC$_2$H$_5$—HC—CH—CHOH—C$_6$H$_5$ with HN-C(=O)-NH ring | 98 |
| nC$_8$H$_{17}$—CH(NH$_2$)—CH(NH$_2$)—CH(OH)—CH$_3$ | nC$_8$H$_{17}$—HC—CH—CHOH—CH$_3$ with HN-C(=O)-NH ring | 96 |
| nC$_8$H$_{17}$—CH(NH$_2$)—CH(NH$_2$)—CH(OH)—C$_6$H$_5$ | nC$_8$H$_{17}$—HC—CH—CHOH—C$_6$H$_5$ with HN-C(=O)-NH ring | 95 |

The spectroscopic and centesimal analysis confirm the structures proposed for these ureas.

It is noteworthy that, under the same conditions, the 1,3-diamino alcohols do not react.

EXAMPLE 25

Direct transformation of diazido alcohols into diazidothiols 1,3-diazido 2-propanethiol synthesis.

The operation is carried out in two steps.

1) Synthesis of the 1,3-diazido 2-chloro propane starting from 1,3-diazido 2-propanol In a 250 ml four-necked bottle equipped with a magnetic stirrer, a thermometer, a cooler, a Mariotte's bulb and containing 2 equivalents of pyridin (2.035 M, 5.54 g) and 1 equivalent of 1,3-diazido 2-propanol (0.035 M), 1.5 equivalent of thionyl chloride (0.053 M, 6.8 g) are very slowly added at 20° C. The reactional medium is then stirred for 12 hours at 50° C. The product is thrown on ice, extracted with methylene chloride, the organic phases are washed with a solution of 10% HCl, dried over MgSO$_4$ and the solvents evaporate.

The chlorine derivative is purified by flash chromatography, the eluant being a 10% mixture of ethyl acetate and petroleum ether.

4.89 g of chlorinated compound are thus isolated, i.e. a 87% yield.

2) Transformation into diazidothiol

In a 250 ml four-necked bottle equipped with a magnetic stirrer, a thermometer, a cooler, a Mariotte's bulb and containing 1.5 equivalent of sodium hydrosulfide (0.53 M, 29.43 g), diluted in 50 ml of methylic alcohol freshly distilled, 1 equivalent of 1,3-diazido-2-chloropropane (0.35M) is added at room temperature. The reactional medium is stirred for 72 hours at room temperature. Then 1 equivalent of soda tablet is slowly added. The product is thrown on ice, extracted in chloroform and dried over $MgSO_4$.

The product is then purified by flash chromatography, the eluant being a 10% mixture of ethyl acetate and petroleum ether.

Thus, the diazidothiol is isolated with a 40% yield.

We claim:

1. A process for preparing polyazido alcohols comprising reacting, with a metal azide in an aqueous medium, a polysubstituted oxirane having a nucleofuge group in position β, wherein the oxirane is represented by the formula

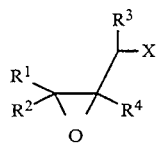

in which X represents a nucleofuge substituent; $R^1$ represents an atom of hydrogen, a lower alkyl group optionally substituted by a halogen, or an aryl group; each of $R^2$ and $R^3$ represents an atom of hydrogen, a lower alkyl radical or an aryl radical; and $R^4$ represents an atom of hydrogen, a lower alkyl group, or an aryl group optionally substituted by an alkoxy group.

2. A process according to claim 1, wherein the metal azide is sodium azide.

3. A process according to claim 1, wherein the nucleofuge group is a halogen atom.

4. A process according to claim 1, wherein the reaction takes place in the presence of a catalyst.

5. A process according to claim 4, wherein the catalyst is selected from the group consisting of quaternary ammonium salts, quaternary phosphonium salts and cryptates.

6. A process according to claim 1, wherein the reaction takes place at a temperature between 20° C. and 100° C.

7. A process according to claim 6, wherein the temperature is 80° C.

8. Diazido alcohols prepared according to the process of claim 2, represented by the formula

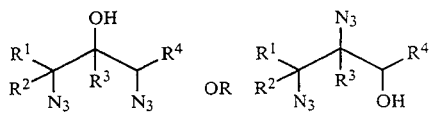

in which $R^1$ represents an atom of hydrogen, a lower alkyl group optionally substituted by a halogen, or an aryl group; each of $R^2$ and $R^3$ represents an atom of hydrogen, a lower alkyl radical or an aryl radical; and $R^4$ represents an atom of hydrogen, a lower alkyl group or an aryl group optionally substituted by an alkoxy group.

9. A method of preparation of polyamino alcohols comprising catalytic hydrogenation of the polyazido alcohols prepared according to claim 1.

10. A method of preparation of ureas comprising reacting the polyamino alcohols prepared according to claim 9 with phosgene.

11. A method of preparation of polyazidothiols comprising adding polyazido alcohols prepared according to claim 1 to thionyl chloride in the presence of pyridine, and then reacting the obtained product with sodium hydrosulfide in the presence of soda and methanol.

12. A process according to claim 5, wherein said catalyst is tricaprylylmethylammonium.

13. A process according to claim 1, wherein all of said alkyl groups are unsubstituted.

14. A process according to claim 1, wherein all of said aryl groups are unsubstituted.

15. A process according to claim 8, wherein all of said alkyl groups are unsubstituted.

16. A process according to claim 8, wherein all of said aryl groups are unsubstituted.

17. A process according to claim 1, wherein the nucleofuge group is a tosylate radical.

18. A process according to claim 1, wherein the nucleofuge group is a mesylate radical.

* * * * *